(12) United States Patent
Rothlin

(10) Patent No.: US 6,797,284 B2
(45) Date of Patent: Sep. 28, 2004

(54) PHYTOPHARMACEUTICAL FOOD PRODUCTS OR INTEGRATORS

(76) Inventor: Ursula Mariah Rothlin, Via Boezio 16, I-00192 Rome (IT)

( * ) Notice: Subject to any disclaimer, the term of this patent is extended or adjusted under 35 U.S.C. 154(b) by 0 days.

(21) Appl. No.: 10/014,935

(22) Filed: Dec. 11, 2001

(65) Prior Publication Data

US 2002/0090441 A1 Jul. 11, 2002

(30) Foreign Application Priority Data

Dec. 12, 2000 (IT) .................................... MI2000A2665

(51) Int. Cl.⁷ .............................................. A01K 35/78
(52) U.S. Cl. ...................... 424/725; 514/553; 562/557; 562/445; 562/559; 562/444; 548/496; 548/344
(58) Field of Search ................................. 424/725, 600

(56) References Cited

U.S. PATENT DOCUMENTS

| | | | |
|---|---|---|---|
| 3,820,548 A | | 6/1974 | Buchmann et al. |
| 3,883,672 A | | 5/1975 | Bone et al. |
| 5,132,113 A | * | 7/1992 | Luca |
| 5,308,627 A | * | 5/1994 | Umbdenstock, Jr. |
| 5,578,307 A | * | 11/1996 | Wunderlich et al. |
| 5,895,652 A | * | 4/1999 | Giampapa |
| 6,132,724 A | * | 10/2000 | Blum |

OTHER PUBLICATIONS

Souchi:Fachmann; Kraut: "Food Composition and Nutrition Tables" 2000 Medpharm Scientific Publishers, Stuttgart, Germany, pp. 823,863,868,876–877, 1123.

* cited by examiner

Primary Examiner—Francisco Prats
Assistant Examiner—Susan D. Coe
(74) Attorney, Agent, or Firm—Herbert Dubno; Jonathan Myers

(57) ABSTRACT

Phytopharmaceutical food products which contain plant extracts and aminoacids and which can be used in order to reduce tobacco smoke addiction.

3 Claims, No Drawings

PHYTOPHARMACEUTICAL FOOD PRODUCTS OR INTEGRATORS

The present invention refers to phytopharmaceutical food products or integrators, that is, products which contain natural extracts of officinal plants.

In particular the present invention refers to products of the type indicated as being suitable for fighting smoke addiction. At the moment patients who are trying to stop smoking are given nicotine and bupropion, which are often found to be necessary in order to overcome craving crises due to the lack of nicotine intake given by cigarettes.

Nevertheless, products of the type indicated which help in the fight against smoke addiction, do not exist at the moment neither as a preventative decreasing the desire for cigarettes, nor as a follow-up as help in therapies which use nicotine and bupropion.

The technical task which the present invention sets itself is, therefore, that of eliminating the complained about technical drawbacks of the prior art, by creating phytopharmaceutical food products or integrators which allow the number of cigarettes smoked to be reduced.

In this technical task one of the, aims of the invention is to create products which can be used as adjuvants in the therapies of patients who are trying to give up smoking.

For example, the products which are the object of the present invention encourage the elimination of toxic substances from the blood, helping the smoker to fight the addiction, and help to maintain the integrity of the internal organs, which is an essential condition in giving up smoking.

Another objective of this invention is that of creating products which have a high concentration and which can be delivered in spray or drop form, in order to render their effect particularly effective.

A further purpose of the invention is that of creating products which can reintegrate the elements which are destroyed or damaged because of smoking, in particular trace elements and/or vitamins.

The last but not least purpose of the invention is that of creating products which are capable of restoring the balance and psycophysical capacity of the person.

For example, the products which are the object of the invention alleviate tension and stress due to the absence of nicotine, increasing concentration, exercising control on the appetite and guaranteeing a tonic help to the neurovegetative system.

The technical task, as well as these and other purposes, according to the present invention are achieved by creating phytopharmaceutical food products, characterised in that they contain plant extracts and aminoacids, and by the fact that they can be used to reduce tobacco smoke addiction.

Other characteristics of the present invention are defined, moreover, in the following claims.

Further characteristics and advantages of the invention will be more evident from the description of the following preferred but not exclusive embodiments of phytopharmaceutical food products and of the integrators according to the finding.

Phytopharmaceutical products according to the finding contain a plurality of fluid components mixed together.

Mainly, such physiotherapeutic products contain plant extracts and aminoacids and are used to reduce tobacco smoke addiction.

Such products contain at least 50% by weight of plant extracts and, in preferred examples, as will become clear later, contain a quantity of plant extracts comprised between 45% and 85%.

The product contains aminoacids of up to 30% of its own weight and preferably the percentage of aminoacids is comprised between 10% and 20%.

In a particularly advantagious example the aminoacids are comprised between 13% and 17% by weight of the product.

The product contains, moreover, an agent such as sorbitol, making up less than 10% and preferably making up between 4% and 6%.

Furthermore, the product contains water in quantities of less than 20% of its own weight and, preferably, comprised between 12% and 18%.

Some products also include natural aromas in percentages of below 1%, preferably under 0.5% and even more preferably between 0.2% and 0.4%.

Moreover, some products include trace elements in percentages of under 10%, and/or hormones in percentages of under 10%, and/or proteins in percentages of under 10%, and/or bioflavonoids in percentages of under 10%, and/or provitamins in percentages of under 10%.

Hereafter, some examples of products according to the finding and their relative applications are described.

EXAMPLE 1

In the first example the product according to the finding includes:

Plant Extracts:
  *arctium lappa,* in weight percentage 15%;
  *silybum marianum,* in weight percentage 30%;
  *gentian lutea,* in weight percentage 10%;
  *vitis vinifera,* in weight percentage 5%;
  *ruscus aculeatus,* in weight percentage 5%;

Aminoacids:
  cysteinea, in weight percentage 15%;

Sorbitol, in Weight Percentage 5%;

Water, in Weight Percentage 15%.

The present product is a phytopharmaceutical concoction which helps to rid the body of toxic substances in general.

Improvement of blood circulation helps the smoker to fight the smoking addiction.

The blood becomes more fluid and more oxygenated helping concentration and mental awareness.

The aminoacid intervenes increasing the detoxifying action of the plant extracts.

EXAMPLE 2

In the second example the product according to the finding includes:

Plant Extracts:
  *escolsica californica,* in weight percentage 25%;
  *matricaria chamomilla,* in weight percentage 25%;
  *tilia cordata,* in weight percentage 5%;
  *crategus oxyacantha,* in weight percentage 7,5%;
  *foeniculum vulgaris,* in weight percentage 2,5%;

Aminoacids:
  phenylalanin, in weight percentage 15%;

Sorbitol, in Weight Percentage 5%;

Water, in Weight Percentage 15%.

The present product is a phytopharmaceutical concoction which helps the smoker in confronting craving attacks.

The preparation is also an adjuvant which alleviates nervous tension and stress due to the lack of nicotine.

The aminoacid in synergy with the plant extracts makes it possible to have better mental concentration, keeps a check on appetite and guarantees tonic help to the neurovegetative system.

Furthermore the product also stimulates the production of endorphins.

EXAMPLE 3

In the third example the product according to the finding includes:

Plant Extracts:
  *cynara scolimus,* in weight percentage 25%;
  *betula alba,* in weight percentage 10%;

*rheum rabarbarum,* in weight percentage 10%;
*taraxacum officinalis,* in weight percentage 5%;
*citrus bigaradia,* in weight percentage 5%;
*foeniculum vulgaris,* in weight percentage 10%;
Aminoacids:
   methionine, in weight percentage 15%;
Sorbitol, in Weight Percentage 5%;
Water, in Weight Percentage 15%.

The present product is a phytopharmaceutical concoction with purifying effects on the internal organs, this being an essential condition for giving up smoking.

The lymphatic circulation is stimulated and, with it, also the elimination of toxins absorbed from the cigarette smoke.

The aminoacid attacks the free radicals and carries out a highly detoxifying role against the catabolites (waste products) of the toxic substances (also against heavy metals).

EXAMPLE 4

In the fourth example the product according to the finding includes:
Plant Extracts:
   *melissa officinalis,* in weight percentage 15%;
   *escolsica californica,* in weight percentage 15%;
   *matricaria chamomilla,* in weight percentage 15%;
   *ruscus aculeatus,* in weight percentage 15%;
   *foeniculum vulgaris,* in weight percentage 10%;
   *silybum marianum,* in weight percentage 10%;
Aminoacids:
   triptophane, in weight percentage 3,75%;
   phenylalanin, in weight percentage 3,75%;
   tyroxine, in weight percentage 3,75%;
   metionine, in weight percentage 3,75%;
Sorbitol, in Weight Percentage 4,7%;
Natural Aromas, in Weight Percentage 0,3%.

The present product is a phytopharmaceutical concoction composed of officinal plant extracts and aminoacids. The product helps to lessen the desire for a cigarette and to reduce the problems concerning craving attacks, physiological dependency and to restore good functioning of the internal organs.

The aminoacids in synergy help to alleviate the crises due to lack of nicotine, to not eat more food than necessary, to lessen nervous tension, to balance the production of central and periferal mediators and to rebuild the psycological balance which has been compromised by smoking.

The product, moreover, is useful above all in people who are trying to stop smoking using methods which use nicotine and bupropion and any other system.

Without physiological support, indeed, the results are usually unsatisfactory.

The product does not have side-effects and helps to restore the psychophysical state.

EXAMPLE 5

In the fifth example the product according to the finding includes:
Plant Extracts:
   *arctium lappa,* in weight percentage 15%;
   *silybum marianum,* in weight percentage 22%;
   *genziana lutea,* in weight percentage 10%;
   *vitis vinifera,* in weight percentage 5%;
   *ruscus aculeatus,* in weight percentage 5%;
Aminoacids:
   cysteine, in weight percentage 15%;
Sorbitol, in Weight Percentage 5%;
Water, in Weight Percentage 15%;
Trace Elements e Mineral Salts, in Weight Percentage of 8%.

The present product is a phytopharmaceutical concoction which, as well as substantially presenting the characteristics of the product already described in example 1, also allows the re-integration of mineral salts lacking because of smoking, and/or which are no longer able attach themselves in the body.

In other examples the product in example 5 presents histidine, phenylalanine, 1a metionine, glutamic acid as aminoacid.

EXAMPLE 6

In the sixth example the product according to the finding includes:
Plant Extracts:
   *arctium lappa,* in weight percentage 15%;
   *silybum marianum,* in weight percentage 25%;
   *genziana lutea,* in weight percentage 10%;
   *vitis vinifera,* in weight percentage 5%;
   *ruscus aculeatus,* in weight percentage 5%;
Aminoacids:
   cistina, in weight percentage 15%;
Sorbitol, in Weight Percentage 5%;
Water, in Weight Percentage 15%;
Hormones:
   contained in weight percentage of 5%.

The present product is a phytopharmaceutical concoction which, as well as substantially presenting the characteristics of the product already described in example 1, also allows the balance of the metabolic processes and/or the neurovegetative tone of the body to be regulated.

EXAMPLE 7

In the seventh example the product according to the finding includes:
Plant Extracts:
   *arctium lappa,* in weight percentage 15%;
   *silybum marianum,* in weight percentage 21%;
   *genziana lutea,* in weight percentage 10%;
   *vitis vinifera,* in weight percentage 5%;
   *ruscus aculeatus,* in weight percentage 5%;
Aminoacids:
   cistina, in weight percentage 15%;
Sorbitol, in Weight Percentage 5%;
Water, in Weight Percentage 15%;
Protein:
   contained in weight percentage of 9%.

The present product is a phytopharmaceutical concoction which, as well as substantially presenting the characteristics of the product already described example 1, also supplies the body with the elements (proteins) necessary for it to produce aminoacids.

In this way they can supply the body with aminoacids without them being directly present in the product.

EXAMPLE 8

In the eighth example the product according to the finding includes:
Plant Extracts:
   *arctium lappa,* in weight percentage 15%;
   *silybum marianum,* in weight percentage 27%;
   *genziana lutea,* in weight percentage 10%;
   *vitis vinifera,* in weight percentage 5%;
   *ruscus aculeatus,* in weight percentage 5%;
Aminoacids:
   cistina, in weight percentage 15%;
   Sorbitol, in Weight Percentage 5%;
   Water, in Weight Percentage 15%;

Bioflavonoids:
  contained in weight percentage of 3%.

The present product is a phytopharmaceutical concoction which, as well as substantially presenting the characteristics of the product already described in example 1, also allows for the reintegration of bioflavonoids.

EXAMPLE 9

In the ninth example the product according to the finding includes:
Plant Extracts:
  *arctium lappa*, in weight percentage 12%;
  *silybum marianum*, in weight percentage 25%;
  *genziana lutea*, in weight percentage 8%;
  *vitis vinifera*, in weight percentage 5%;
  *ruscus aculeatus*, in weight percentage 5%;
Aminoacids:
  cistina, in weight percentage 15%;
Sorbitol, in Weight Percentage 5%;
Water, in Weight Percentage 15%;
Provitamins and/or Vitamins:
  contained in weight percentage of 10%.

The present product is a phytopharmaceutical concoction which, as well as substantially presenting the characteristics of the product already described in example 1, also allows for the reintegration of vitamins which, in a smoker's body, are lacking because of the smoke.

It has, indeed, been ascertained that phytopharmaceutical food products according to the finding are particularly advantagious both because they allow a reduction in the number of cigarettes smoked, and also because they help in detoxification and smoke addiction.

Furthermore, the products also permit the reintegration of elements necessary for the body, for balance and for psychophysical capacity.

The phytopharmaceutical food products thus conceived are susceptable to numerous modifications and variants, all falling within the scope of the inventive concept; moreover all the details can be replaced with technically equivalent elements.

In fact the materials used, not to mention the sizes, can be whatever according to requirements and the state of the art.

What is claimed is:

1. A method of aiding an individual who smokes, to stop smoking, which comprises the step of administering to said individual a therapeutically effective amount of a phytopharmaceutical composition for reducing tobacco smoke addiction which consists essentially of:
  (a) 10 to 30% by weight of at least one amino acid selected from the group consisting of cysteine, cystine, phenylalanine, methionine, tryptophan, tyrosine, histidine and glutamic acid; and
  (b) 45 to 85% by weight of a mixture of plant extracts wherein the mixture includes:
    (1) *escolsica califormica, matricaria chamomilla, tilia cordata, crategus oxyacantha,* and *foeniculum vulgaris,* or
    (2) *melissa officinalis, escolsica californica, matricaria chamomilla, ruscus aculeatus, foeniculum vulgaris,* and *silybum marianum;* together with a pharmaceutically acceptable inert carrier or diluent.

2. A method of aiding an individual who smokes, to stop smoking, which comprises the step of administering to said individual a therapeutically effective amount of a phytopharmaceutical composition for reducing tobacco smoke addiction which consists essentially of:
  (a) 10 to 30% by weight of at least one amino acid selected from the group consisting of cysteine, cystine, phenylalanine, methionine, tryptophan, tyrosine, histidine and glutamic acid; and
  (b) 45 to 85% by weight of a mixture of plant extracts wherein the mixture includes: *melissa officinalis, escolsica californica, matricaria chamomilla, ruscus aculeatus, foeniculum vulgaris,* and *silybum marianum;* together with a pharmaceutically acceptable inert carrier or diluent.

3. A method of aiding an individual who smokes, to stop smoking, which comprises the step of administering to said individual a therapeutically effective amount of a phytopharmaceutical composition for reducing tobacco smoke addiction which consists essentially of:
  3.75% by weight tryptophan;
  3.75% by weight phenylalanine;
  3.75% by weight tyrosine;
  3.75% by weight methionine;
  15% by weight *melissa officinalis,*
  15% by weight *escolsica californica;*
  15% by weight *matricaria chamomilla;*
  15% by weight *ruscus aculeatus;*
  10% by weight *foeniculum vulgaria;*
  10% by weight *silybum marianum;* and
  4.7% by weight sorbitol.

* * * * *